United States Patent [19]
Plone

[11] Patent Number: 5,147,337
[45] Date of Patent: Sep. 15, 1992

[54] MEDICAMENT DISPENSER

[76] Inventor: Clifford Plone, 1619 W. Coventry Pl., Palmdale, Calif. 93551

[21] Appl. No.: 734,173

[22] Filed: Jul. 22, 1991

Related U.S. Application Data

[60] Continuation-in-part of Ser. No. 520,276, May 7, 1990, Pat. No. 5,035,320, and a continuation-in-part of Ser. No. 628,147, Dec. 12, 1990, Pat. No. 5,076,425, which is a division of Ser. No. 520,276, May 7, 1990, Pat. No. 5,035,320.

[51] Int. Cl.$^5$ .............................................. A61F 13/00
[52] U.S. Cl. ........................... 604/306; 604/289; 604/310; 206/219; 206/222; 128/743
[58] Field of Search ............... 206/219, 222; 128/743; 604/3, 289, 306, 310

[56] References Cited

U.S. PATENT DOCUMENTS

| | | |
|---|---|---|
| 2,487,236 | 11/1949 | Greenberg . |
| 2,653,610 | 9/1953 | Smith . |
| 2,653,611 | 9/1953 | Smith . |
| 2,805,162 | 9/1957 | Kovel . |
| 2,901,357 | 8/1959 | Epstein . |
| 3,048,317 | 8/1962 | Cochrane et al. . |
| 3,102,465 | 9/1963 | Montesano . |
| 3,116,732 | 1/1964 | Cahill ................................ 604/306 |
| 3,225,915 | 12/1965 | Wise . |
| 3,326,363 | 6/1967 | Bennett et al. . |
| 3,524,566 | 8/1970 | Parks . |
| 3,743,520 | 7/1973 | Croner . |
| 3,796,813 | 3/1974 | Kurland . |
| 3,824,322 | 7/1974 | Fiorella . |
| 3,977,559 | 8/1976 | Lombardi . |
| 3,977,562 | 8/1976 | Wedzik . |
| 3,994,411 | 11/1976 | Elfelt et al. . |
| 4,074,827 | 2/1978 | Labe, III . |
| 4,253,773 | 3/1981 | Aho et al. . |
| 4,264,007 | 4/1981 | Hunt . |
| 4,333,583 | 6/1982 | Montemarano . |
| 4,387,809 | 6/1983 | Botzler . |
| 4,399,158 | 8/1983 | Bardsley et al. . |
| 4,430,013 | 2/1984 | Kaufman ............................... 604/3 |
| 4,524,078 | 6/1985 | Bardsley et al. . |
| 4,596,713 | 6/1986 | Burdette . |
| 4,627,986 | 12/1986 | Bardsley et al. . |
| 4,634,003 | 1/1987 | Ueda et al. . |
| 4,689,044 | 8/1987 | Murata ............................... 604/306 |
| 4,785,931 | 11/1988 | Weir et al. . |
| 4,808,172 | 2/1989 | Murata ............................... 604/306 |
| 4,821,875 | 4/1989 | Groves et al. . |
| 4,860,929 | 8/1989 | Lowe et al. . |
| 4,871,555 | 10/1989 | Schwartz et al. . |
| 4,891,232 | 1/1990 | Dahl . |
| 4,927,283 | 5/1990 | Fitjer .................................. 604/3 |
| 4,935,018 | 6/1990 | Scholz ............................... 604/289 |
| 5,030,214 | 7/1991 | Spector ............................. 604/289 |
| 5,035,320 | 7/1991 | Plone ................................ 206/219 |

Primary Examiner—Randall L. Green
Assistant Examiner—Paul Prebilic
Attorney, Agent, or Firm—William W. Haefliger

[57] ABSTRACT

A medicament dispenser comprising carrier structure; elongated pusher structure on the carrier structure; elongated receptacle structure beneath the pusher structure and on the carrier structure, there being an elongated zone or zones between the pusher structure and receptacle structure to receive dispensable medicament substance or substances; the pusher structure being selectively manually deflectable toward the receptacle, at selected locations along pusher structure length; the receptacle structure being porous at selected lengthwise locations corresponding to the selected pusher structure locations, and in response to downward deflection of the pusher structure; whereby dispensing of dispensable medicament substance or substances occurs at locations corresponding to selected deflected locations of the pusher structure.

8 Claims, 13 Drawing Sheets

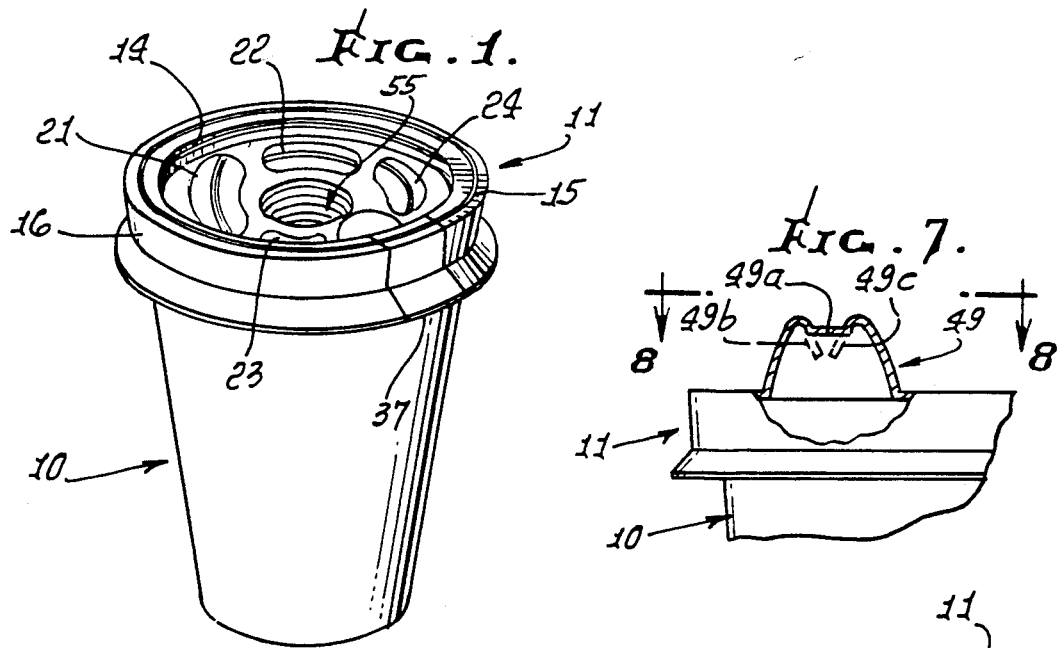
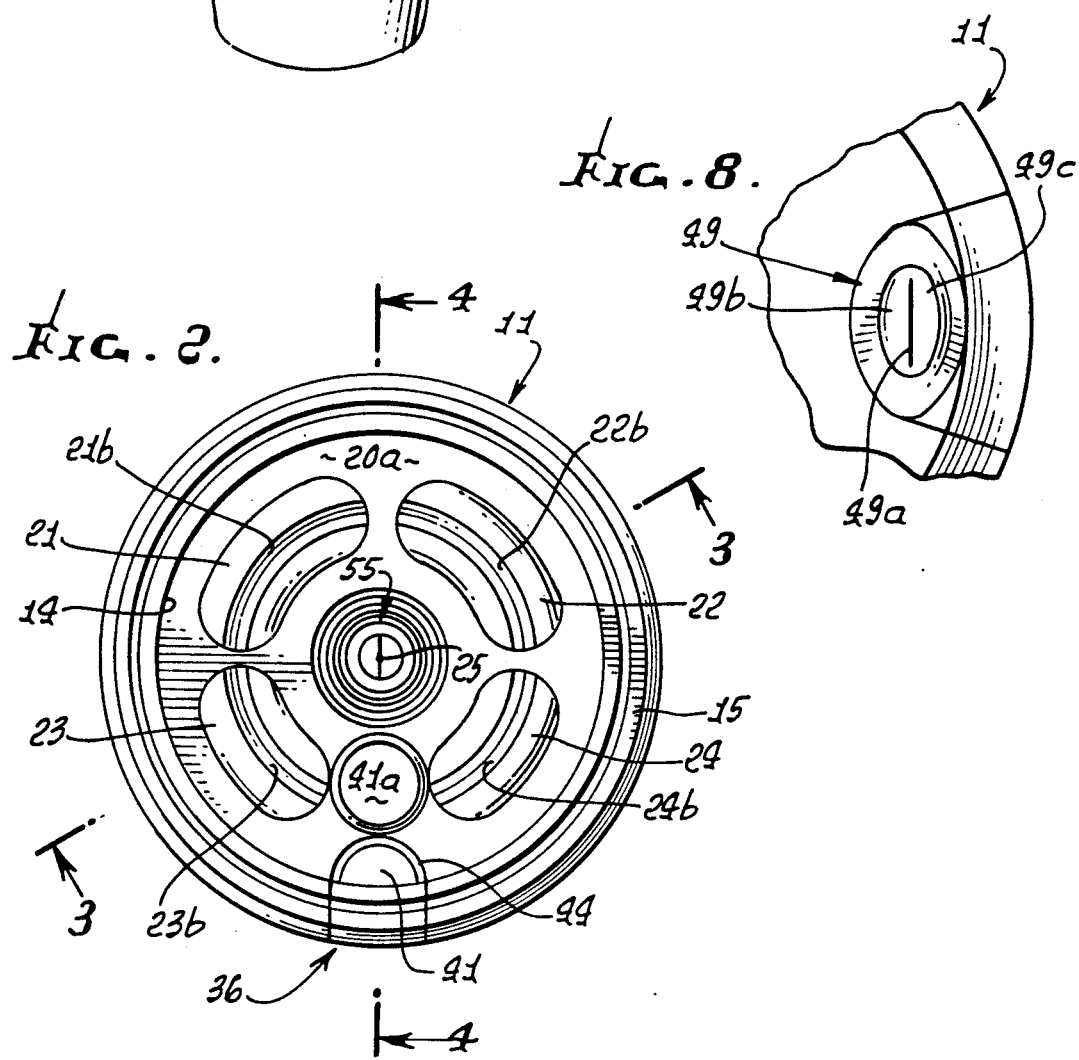

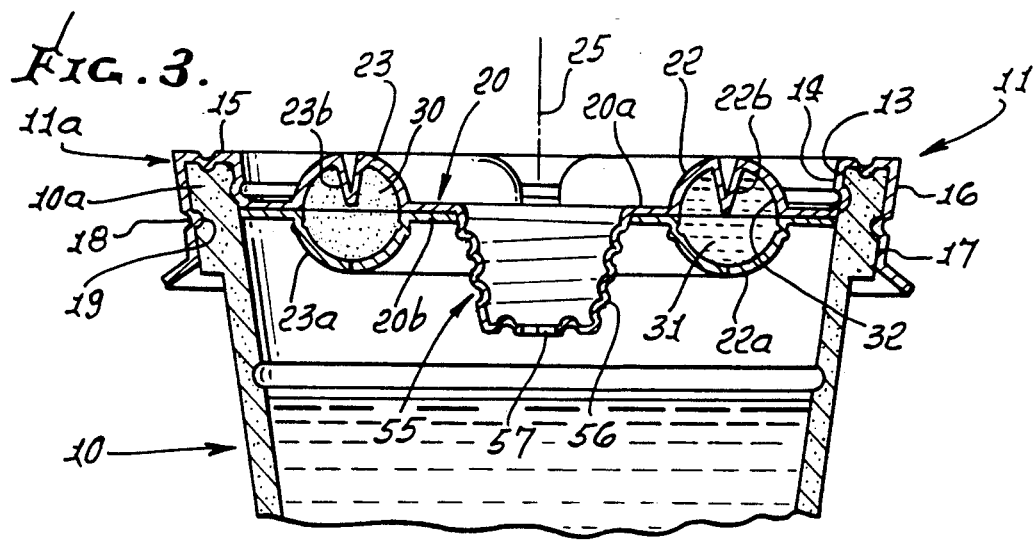
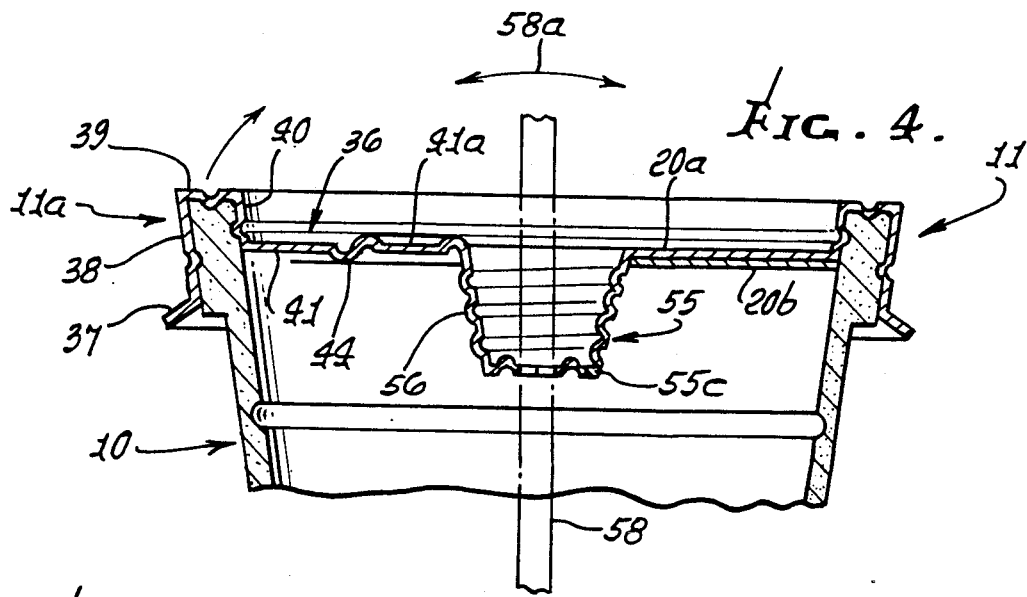
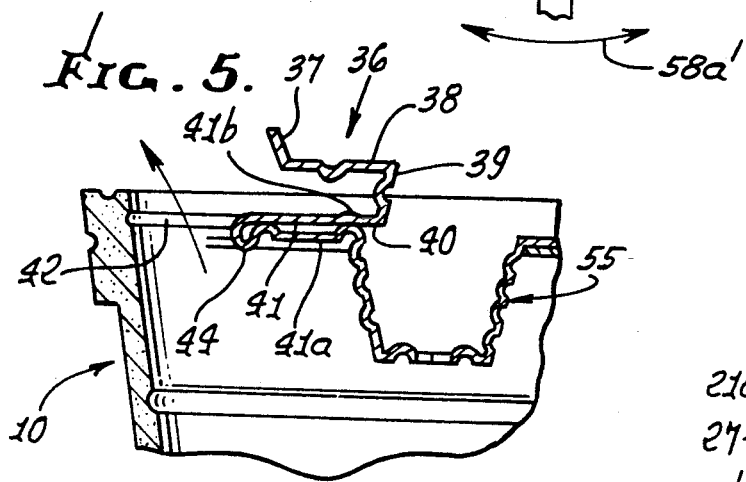
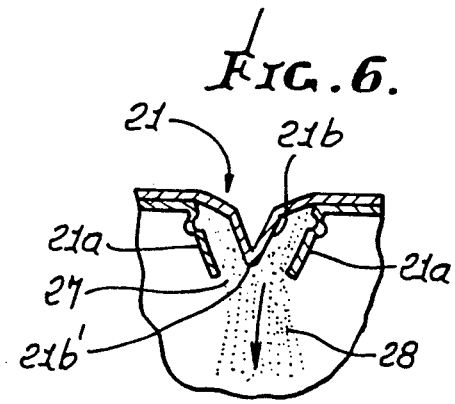

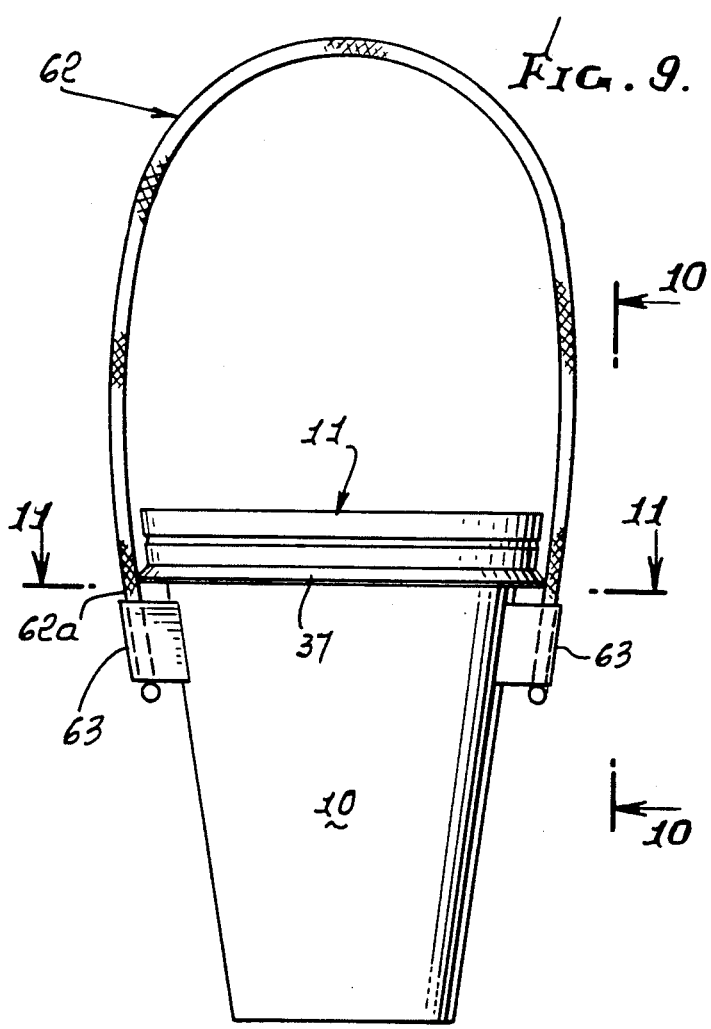
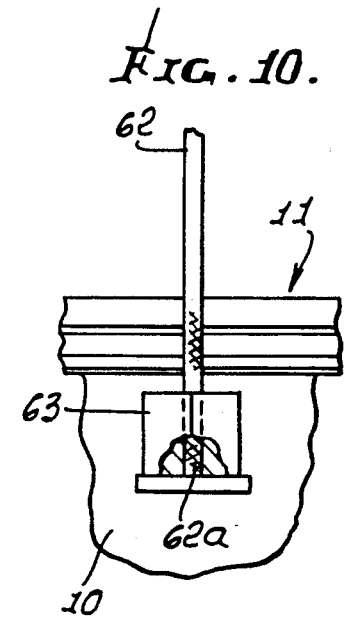
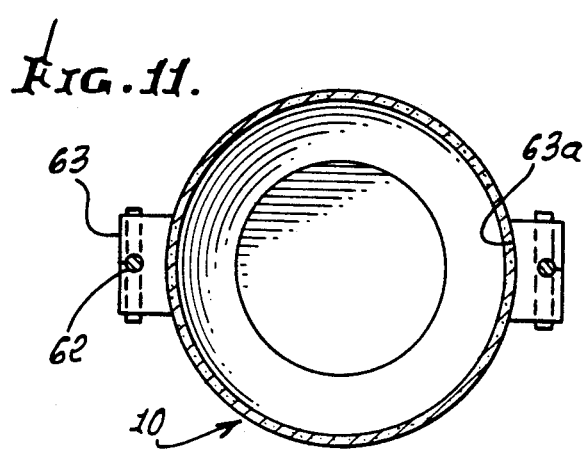
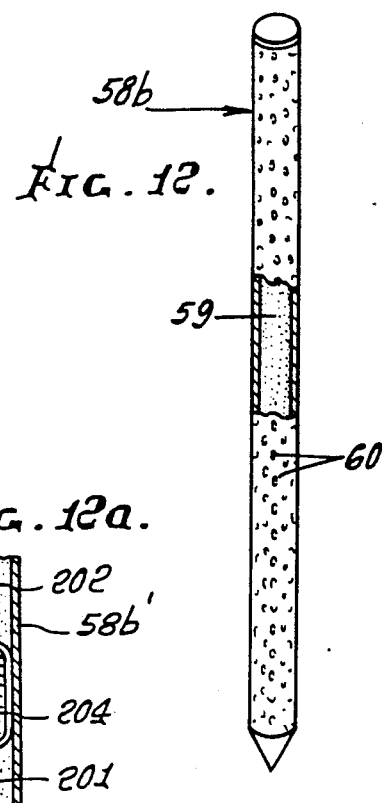
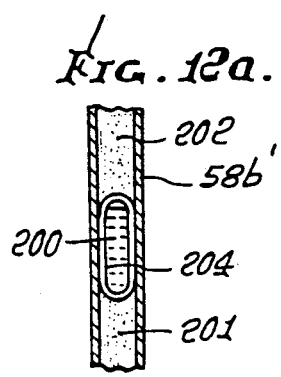

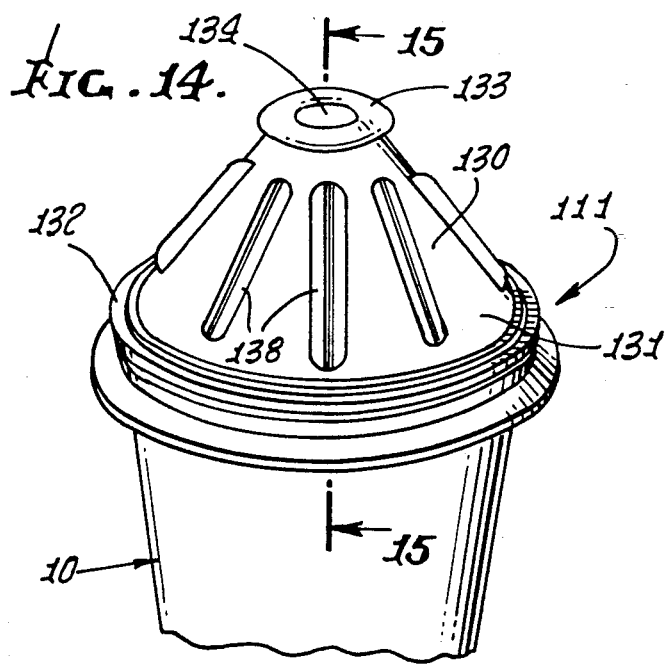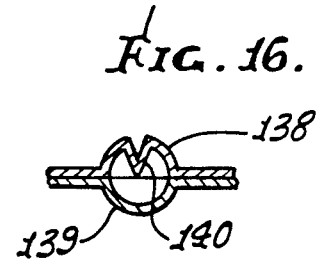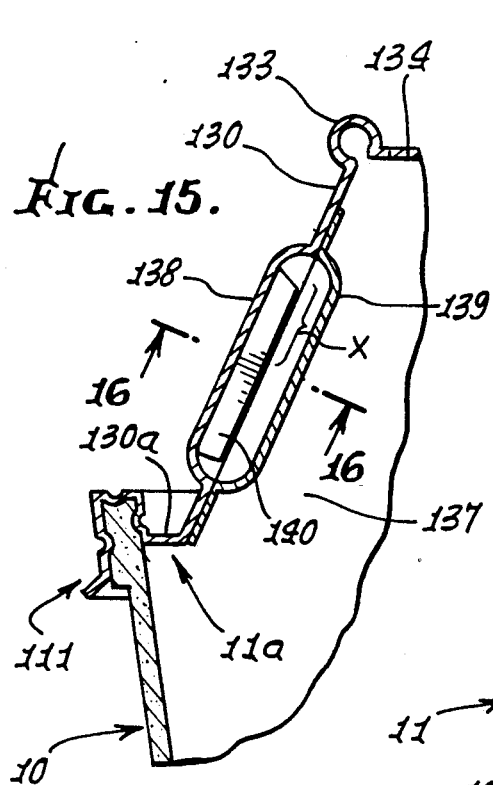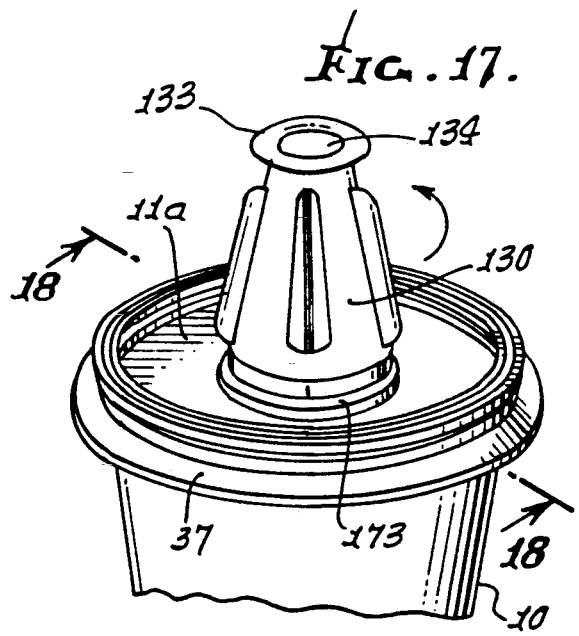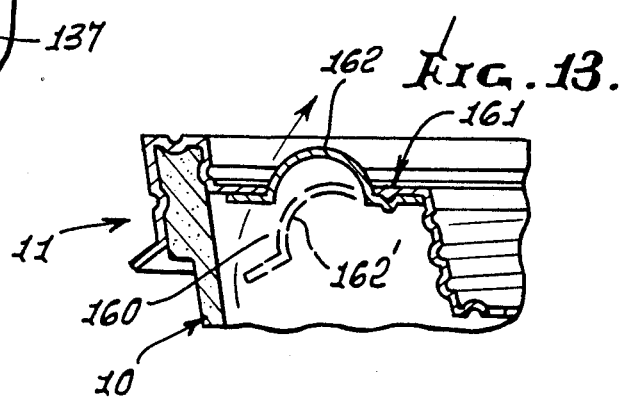

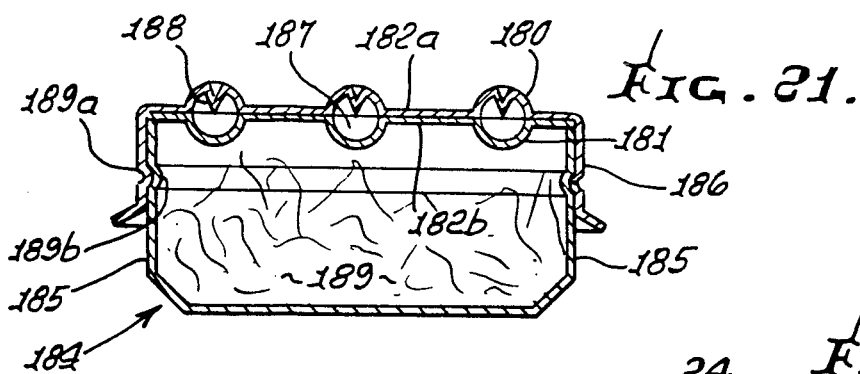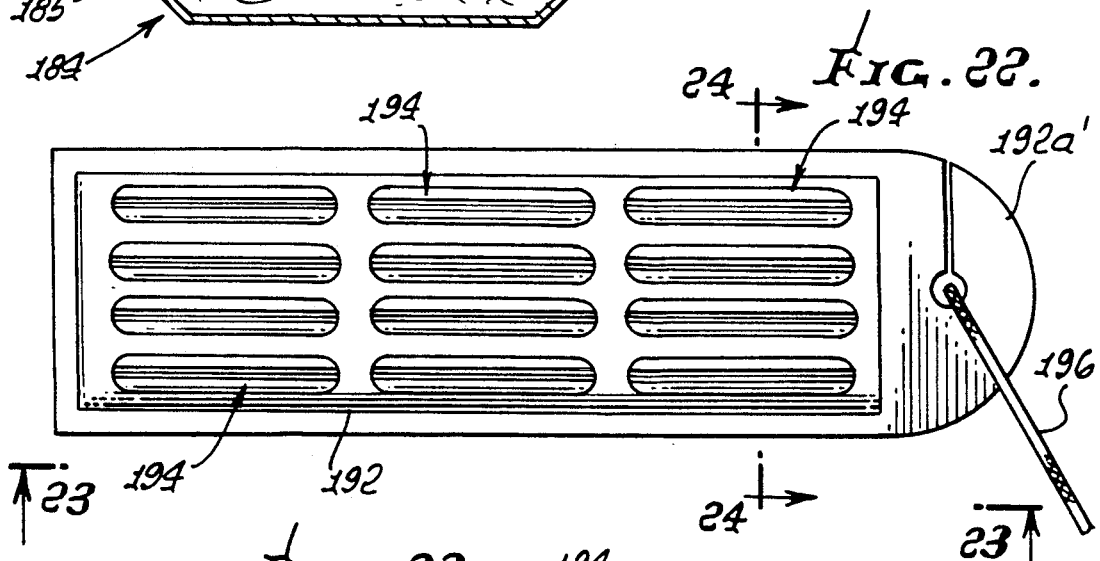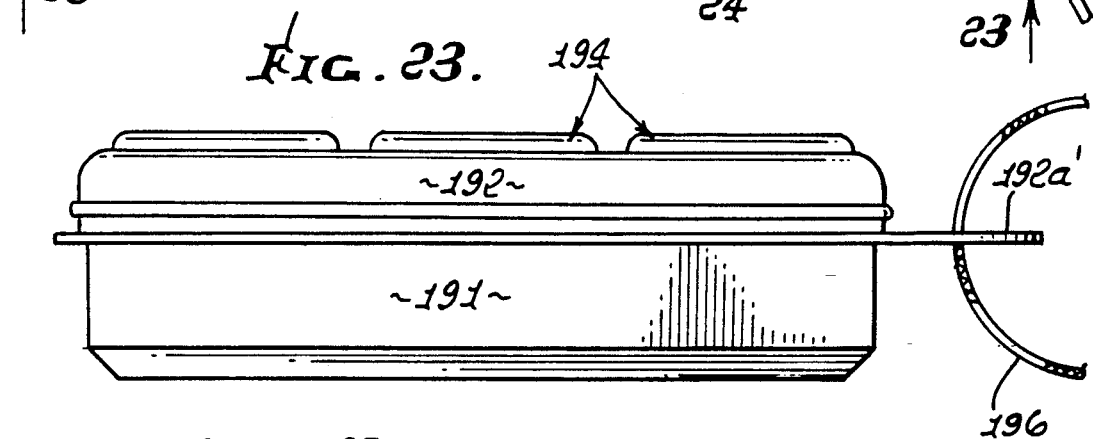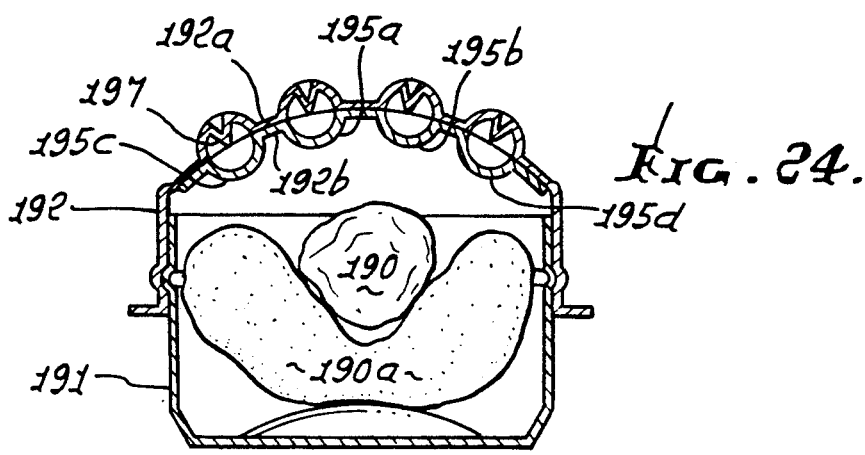

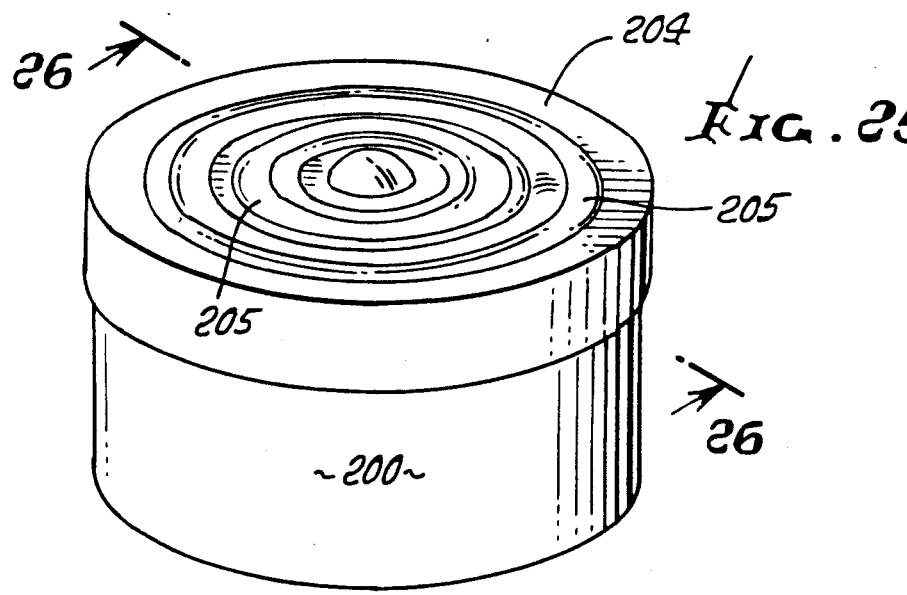
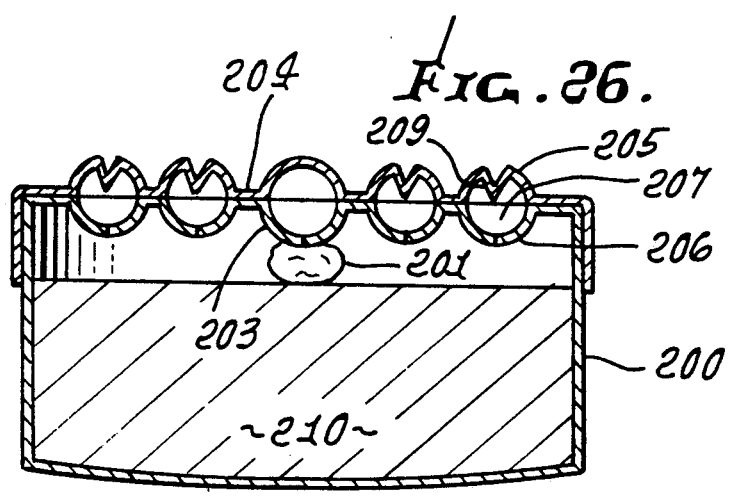
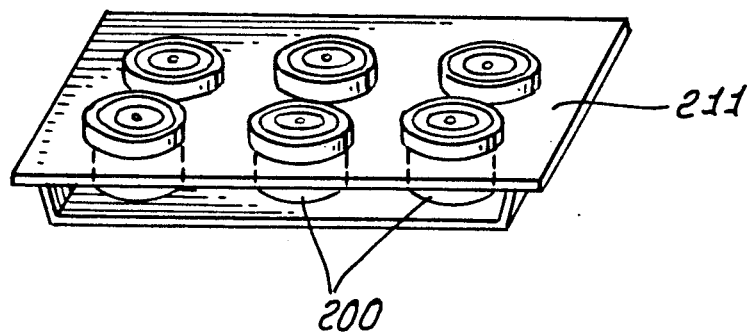

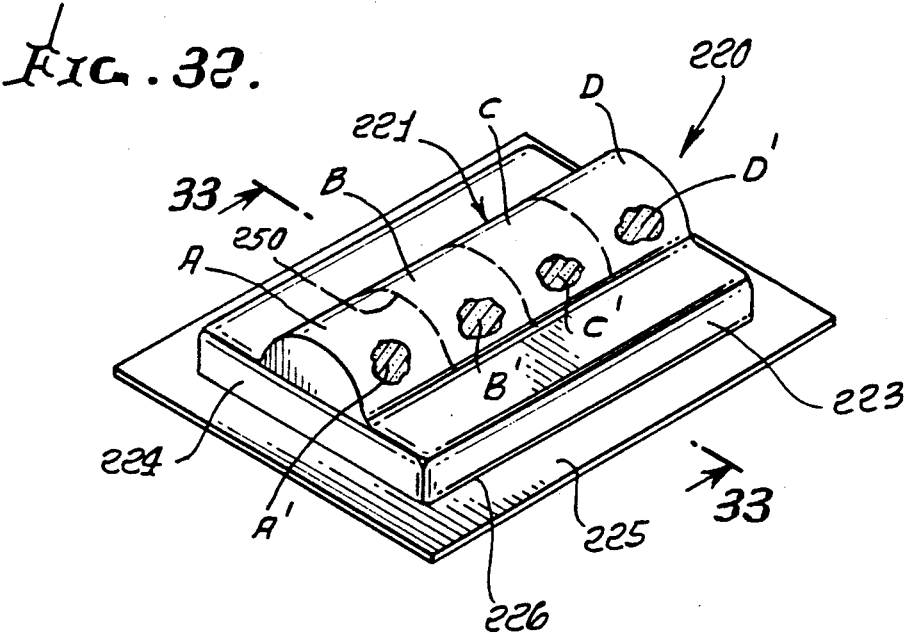
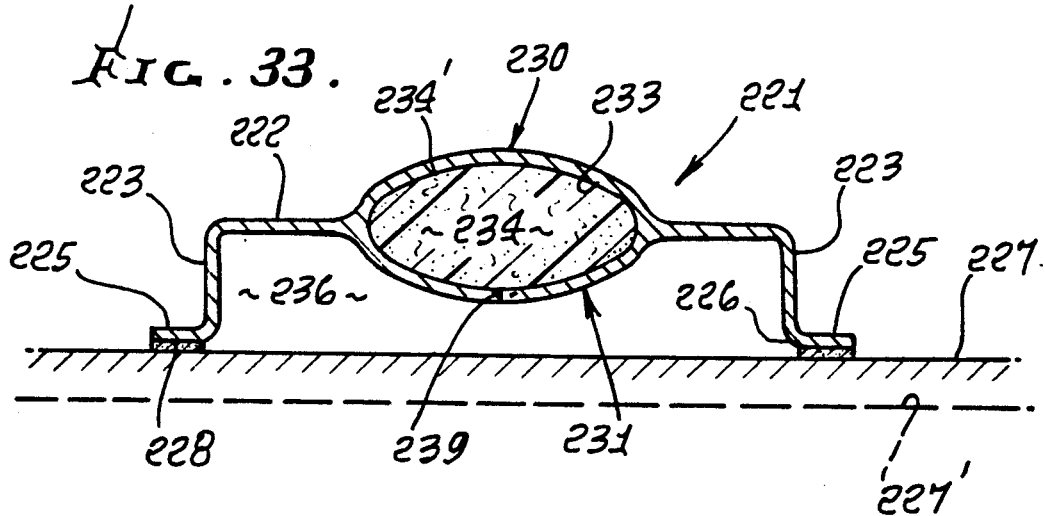
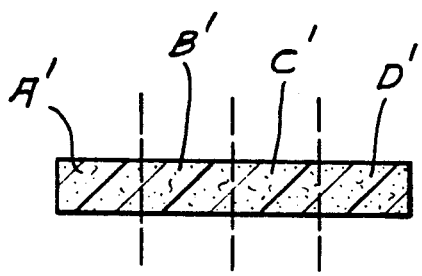

MEDICAMENT DISPENSER

BACKGROUND OF THE INVENTION

This application is a continuation-in-part of Ser. No. 520,276 filed May 7, 1990 now U.S. Pat. No. 5,035,320, and is a continuation-in-part of Ser. No. 628,147 filed Dec. 12, 1990 now U.S. Pat. No. 5,076,425, which is a division of Ser. No. 520,276 filed May 7, 1990, now U.S. Pat. No. 5,035,320.

This invention relates generally to dispensers for dispensing flowable or liquid medicament substances; and more particularly concerns simple, effective, manually manipulable dispensers for such flowable or liquid substances retained on carriers applicable to the skin or other surface of a user.

The application of medicaments to the surface or skin of a user creates problems which include how to controllably dispense the substance on a bandage or dressing, how to re-supply the medicament without removing the bandage or dressing, and how to accurately control such re-supply.

The problem becomes acute when removal of the bandage might remove regrowth skin or tissue, as in burn treatment. There is need for simple, effective means to controllably dispense or disperse medicament substance or substances to a skin or other surface area, while protected as via a bandage or other dressing.

SUMMARY OF THE INVENTION

It is a major object of the invention to provide a solution to the above problem and difficulties. Basically, the invention relates to a medicament dispenser comprising:

a) carrier means, b) elongated pusher means on the carrier means, c) elongated receptacle means beneath the pusher means and on the carrier means, there being an elongated zone or zones between the pusher means and receptacle means to receive dispensable medicament substance or substances, d) the pusher means being selectively manually deflectable toward the receptacle, at selected locations along pusher means length, e) the receptacle means being porous at selected lengthwise locations corresponding to the selected pusher means locations, and in response to downward deflection of the pusher means, f) whereby dispensing of dispensable medicament substance or substances occurs at locations corresponding to selected deflected locations of the pusher means.

As will be seen, the carrier may comprise a holder applicable to a user's surface to be treated. Typically, the carrier means comprises a flap means having adhesive thereon to adhere to the skin of a user, in laterally spaced relation to the referenced zone or zones. The attachment flap means in this regard may be connected to or extend from carrier body portions extending downwardly and protectively at the sides of the zones referred to.

It is another object to provide pusher and receptacle means on a dome portion of the carrier that projects upwardly above the level of the flap means, the zone or zones being hollow to receive and confine the medicament substance passed downwardly from a selected portion or portions of the receptacle means. A medicament-containing sponge may be provided between the receptacle means and the pusher means, the sponge being elongated in the direction of elongation of the pusher means. Further, an applicator sponge may be located in the zone or zones below the receptacle means to receive medicament substance via the porous receptacle when the pusher means is pushed downwardly. Both sponges may be elongated in the direction of pusher means elongation, for selective squeezing of selected portions of the medicament-containing sponge and for selective feeding of medicament of the medicament-containing sponge to the applicator sponge.

It is a further object to provide deflector means integral with the pusher means, projecting downwardly along its length toward the receptacle means to deflect and open the receptacle means at selected locations along its length in response to downward deflection of the pusher means, thereby to allow downward passage of substance to selected portions of the user's surface. The deflector means may include walls of the pusher means which taper downwardly along the pusher means length to define an elongated penetrator or penetrators. Alternatively, the receptacle means may have or contain small vent openings to pass the medicament substance along its length.

Yet another object is to provide different medicaments in different portions of the elongated space between the pusher and receptacle, as in different portions of a dispenser sponge in that space to be selectively squeezed.

A further object is to provide the carrier means in the form of an elongated handle, the pusher means and receptacle means being elongated in the direction of handle elongation, the handle having a hollow interior. An applicator may be carried by the elongated handle to receive medicament from the hollow interior of the handle; and that applicator may comprise a sponge or flexible strands, such as a puff. Gate means may be located between the handle interior and the applicator to gate medicament flow toward the applicator; and two such gates may be provided to enable flow of measured amounts of medicament toward the applicator.

These and other objects and advantages of the invention, as well as the details of an illustrative embodiment, will be more fully understood from the following specification and drawings, in which:

DRAWING DESCRIPTION

FIG. 1 is a perspective view of a dispenser top or cap on an associated drinking cup;

FIG. 2 is a plan view of the FIG. 1 dispenser top;

FIG. 3 is a section taken on lines 3—3 of FIG. 2;

FIG. 4 is a section taken on lines 4—4 of FIG. 2;

FIG. 5 is a fragmentary view like FIG. 4 showing a drinking zone of the dispenser top in opened condition;

FIG. 6 is a fragmentary view showing pusher and receptacle mean on the top in downwardly displaced condition;

FIG. 7 is a fragmentary view of a modified drinking means on the FIG. 1 dispenser top;

FIG. 8 is a plan view taken on lines 8—8 of FIG. 7;

FIG. 9 is an elevation showing a handle on the cup as shown in FIG. 1;

FIG. 10 is a fragmentary elevation taken on lines 10—10 of FIG. 9;

FIG. 11 is a section taken on lines 11—11 of FIG. 9;

FIG. 12 is a perspective view of a mixing tube which contains substance to be dispensed into the cup;

FIG. 13 is a view like FIG. 7 showing a modified drinking means on a dispenser top;

FIG. 14 is a view like FIG. 1 showing a modified dispenser top or cap on a drinking cup;

FIG. 15 is an enlarged section taken in elevation on lines 15—15 of FIG. 14;

FIG. 16 is a section taken on lines 16—16 of FIG. 15;

FIG. 17 is a view like that of FIG. 14 showing yet another modified dispenser top or cap with a central drinking means on a drinking cup;

FIG. 21 is a section taken in elevation on lines 21—21 of FIG. 20 showing the dispenser above salad in a tray;

FIG. 22 is a plan view like FIG. 20 showing a modified dispenser above a wiener and bun in a tray;

FIG. 23 is a side view elevation taken on lines 23—23 of FIG. 22;

FIG. 24 is a sectional elevation taken on lines 24—24 of FIG. 22;

FIG. 25 is a view like FIG. 1 showing an additional modified cap or top on an ice cream container;

FIG. 26 is an elevation taken in section on lines 26—26 of FIG. 25;

FIG. 27 is a perspective view showing multiple of the containers, and their tops, as in FIG. 25, on a support;

FIG. 32 is a perspective view of the invention as applied to a medicament dispenser;

FIG. 33 is an enlarged section taken on lines 33—33 of FIG. 32;

FIG. 34 is a plan view of an elongated medicament supply sponge, sectioned to supply different medicaments;

DETAILED DESCRIPTION

Figure 18:
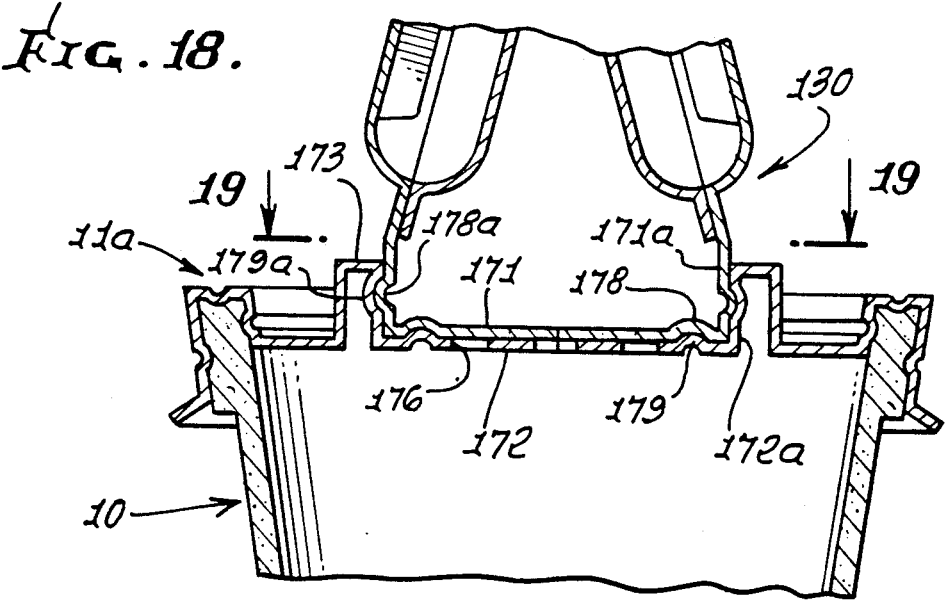
FIG. 18 is an enlarged section taken on lines 18—18 of FIG. 17.
Figure 19:
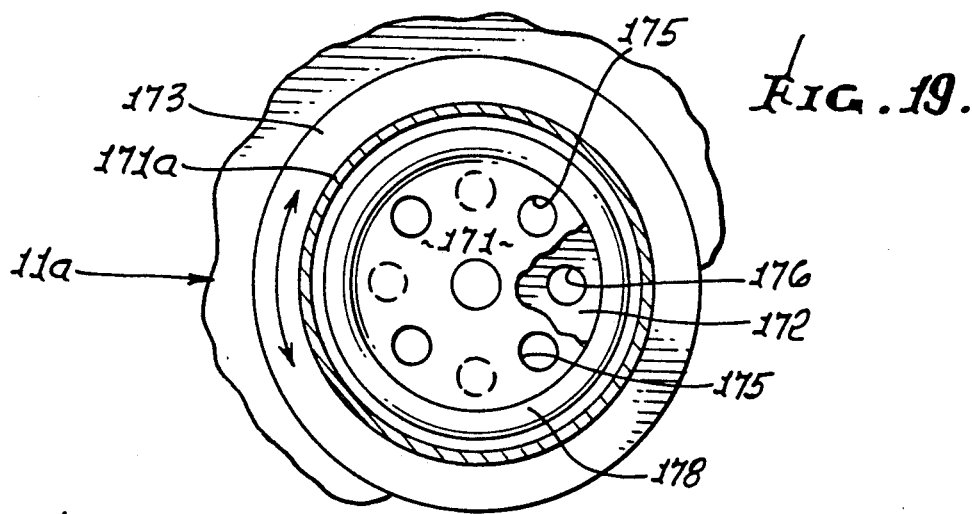
FIG. 19 is a horizontal section taken on lines 19—19 of FIG. 18.

Since the invention is related to that of the U.S. patent applications referred to above, those systems will first be described.

In FIGS. 1-6, a drinking cup 10 is provided with a carrier in the form of a cap 11. The cap or lid includes an outer portion 11a that interfits the upper rim portion 10a of the cup, which may for example consist of molded plastic material, such as styrofoam. Note that lid outer portion 11a may have an inner annular wall 14 that extends upwardly adjacent the cup inner wall 13, a top wall 15 that extends over the cup rim, and an outer wall 16 that extends downwardly adjacent the cup rim outer wall 17. Detented portions of these lid walls may interfit correspondingly detented portions of the cup wall, as at 18 and 19, for example, to form a rim seal.

The lid or cap also includes pusher means on the disc portion or wall 20, as well as receptacle means on that wall 20. See for example the multiple, arcuately elongated pushers 21, 22, 23, and 24 which extend upwardly and about the upright axis 25, and the corresponding multiple, arcuately elongated, receptacles 21a, 22a, 23a, and 24a which extend downwardly and about axis 25 directly beneath the pushers. The pushers are integral with an upper layer 20a of the wall 20, and the receptacles are integral with a lower layer 20b of the wall 20, the two layers typically being separately molded of plastic material and bonded together at their interface. Deflectors 21b-24b are respectively carried by, and are integral with, the pushers to project downwardly toward the receptacles to deflect and open the receptacles when the pushers are selectively pushed or displaced downwardly. See for example FIG. 6 showing a flexible pusher 21 displaced downwardly (manually) to cause a deflector 21b to split open, at 27, a thin walled, frangible receptacle 21a so that the contents 28 of the receptacle can drain or fall into the liquid in the cup 10. Different receptacles contain different additives (for the liquid), such as sugar and cream (or other), to be added to coffee or tea (or other) in the cup. See sugar at 30 and cream at 31 in FIG. 3.

Each pusher and its receptacle define an interior zone, as at 32, separated from the interior zone of other pushers and their receptacles. Further, each pusher and its receptacle are arcuately elongated so that the user can run his finger along the pusher to desired extent corresponding to the amount of additive to be added into the liquid in the cup. This is particularly effective in the case of sugar, which tends to fall primarily from that portion of the receptacle which is split open by the deflector. The latter tapers downwardly toward an edge tip as at 21b', and which variably splits open the receptacle to the extent that the user's finger is pushed downwardly directly over that deflector. Note that pushers 21 and 22 may extend over zones which contain sugar, and pushers 23 and 24 may extend over cream-containing zones. Thus, the receptacle means, being frangible, is pushed open at selected lengthwise locations that correspond to the selected deflected pusher means locations, and in response to local deflection of the pusher means.

Note also the provision of a zone on the lid adapted to be opened to define a drinking access means, for passing liquid from the container interior through the lid on the container. See for example the local flap zone 36 of the lid in FIGS. 4 and 5. As the local lip 37 of the liftable flap is raised, it lifts local wall sections 38–40 of the lid, as well as local cover section 41 of the lid, to the position seen in FIG. 5, exposing opening 42 via which the liquid contents of the cup may be poured, or drunk, as the cup is tilted. See also the local angled portion 44 of the lid which allows flexing at that portion as the flap is raised. That flap is located between pushers 23 and 24 in FIG. 2. Cover section 41 is displaced over cover section 41a in FIG. 5.

A modified drinking access zone is shown in FIGS. 7 and 8 to comprise a local dome section 49 of the lid, as between pushers 23 and 24, and near the cup outer wall. The top of the dome defines a slit 49a via which liquid may be poured or drunk, after push down of dome sections 49b and 49c.

FIGS. 3 and 4 show a central portion of the lid which forms a flexible receptacle 55 projecting downwardly, and having an undulating wall 56. It contains a central opening 57 to pass a mixing stick or rod at 58.

The latter may then be oscillated, manually (see arrows 58a and 58a') due to the flexing wall 56 for mixing of liquid and additives in the container.

In FIG. 12, the mixing stick 58b is tubular and contains substance 59 to be dispensed into liquid in the container 10, as via pores or openings 60 in the tube wall. Tea may, for example, be dispensed into hot water in the container, via water ingress into the stick, and tea-flavored water egress.

FIGS. 9–11 show the apparatus as described, as in FIGS. 1–8, but wherein a flexible U-shaped handle 62 is provided. Lower ends 62a of the handle fit in ears 63 on the wall of the cup or container 10. Those ears may be tapered at 63a to fit the cup without being integral therewith.

In FIGS. 14–16, the carrier or lid 111 for the cup or container s modified and has a central dome portion 130 which tapers upwardly from a region 131 near the annular bead 132 which attaches to the container rim as before. See FIG. 3. The thin-walled dome is frusto-conical and has an annular top 133 like a soft drink bottle top centrally open at 134 for drinking purposes, as when the cup 10 is tilted. The slanting wall of the dome carries or supports pushers 138, and associated receptacles 139 of the same elongated construction as before, except that they are upright and linear, rather than horizontally curved. The dome is hollow, as seen at 137 in FIG. 15, whereby the contents of the receptacles are selectively discharged into that hollow to fall into liquid in the container when the pushers are pushed inwardly toward the hollow. Such pushing causes the deflectors 140 to open up the frangible receptacles and discharge their contents via the opened up slit cut by the deflector. If only that upper portion of the deflector indicated at "x" in FIG. 15 cuts into and opens a deflector, then only that much of the receptacle contents spills into the container, whereby the amount of used sugar, cream, etc., may be accurately controlled. The pushers are on lid or cap wall section 130a, integral with conical wall 130, and the receptacles are on section 130b attached to 130. Section 130a joins lid outer portion 11a.

FIG. 13 shows a modified drinking access opening 160 provided in the lid 161 when a tab 162 is pushed downwardly to position 162'. The lid is of the form seen in FIGS. 1–8.

FIGS. 17 and 18 show another modified form, similar to FIGS. 14 and 15, but wherein the carrier includes additional upper and lower carrier sheets extending horizontally in adjacent relation to form the lid, one additional carrier sheet carrying the dome portion of the carrier, and the other additional carrier sheet connectible to the container, the sheets having registrable openings therein, and the upper additional sheet rotatable relative to the lower additional sheet to selectively register the openings. See for example in FIG. 18 the additional and rotary upper carrier sheet 171, and the additional and non-rotary lower carrier sheet 172, extending horizontally in superposed relation. Sheet 171 carries the dome portion 130, as described above, as via upright annular peripheral wall 171a connected to or integral with wall 130a; and the lower carrier sheet 172 has an upright annular wall 172a joined at 173 to the lid outer portion 11a. Upright wall 172a rotatably centers the upright wall 171a as the latter is rotated. Such rotation, effected manually by rotating the dome 130, brings openings 175 in upper carrier sheet 171 into vertical registration with openings 176 in the lower carrier sheet 172 for passing the substances selectively discharged into the central hollow 137, as by manipulation of the pusher or pushers. Note also the top 133, open at 134, for drinking. Note guide ribs 178 and 179, which annularly nest, and ribs 178a and 179a which nest and retain the wall 171 adjacent wall 172.

Figure 20:
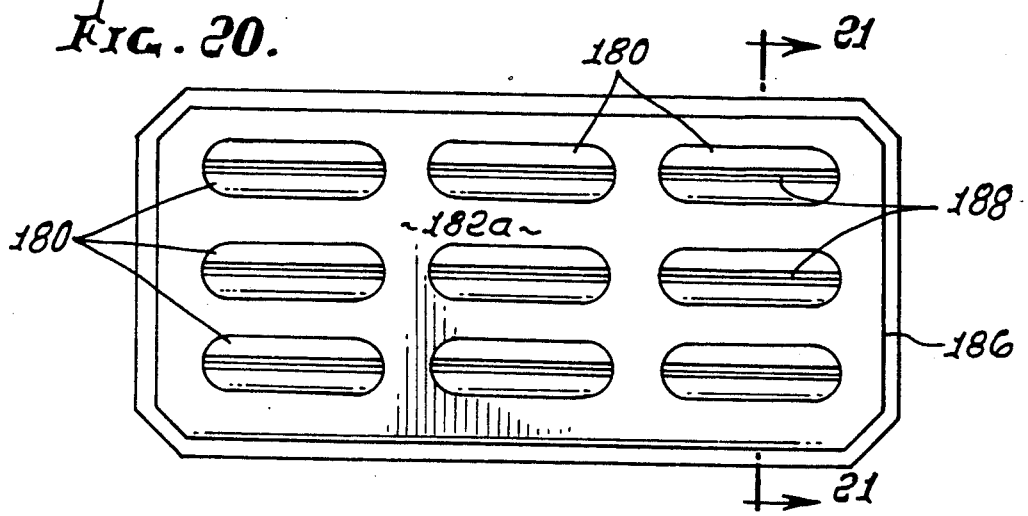
FIG. 20 is a plan view of a further modified dispenser cap or top, as for use on a tray.
Figure 28:
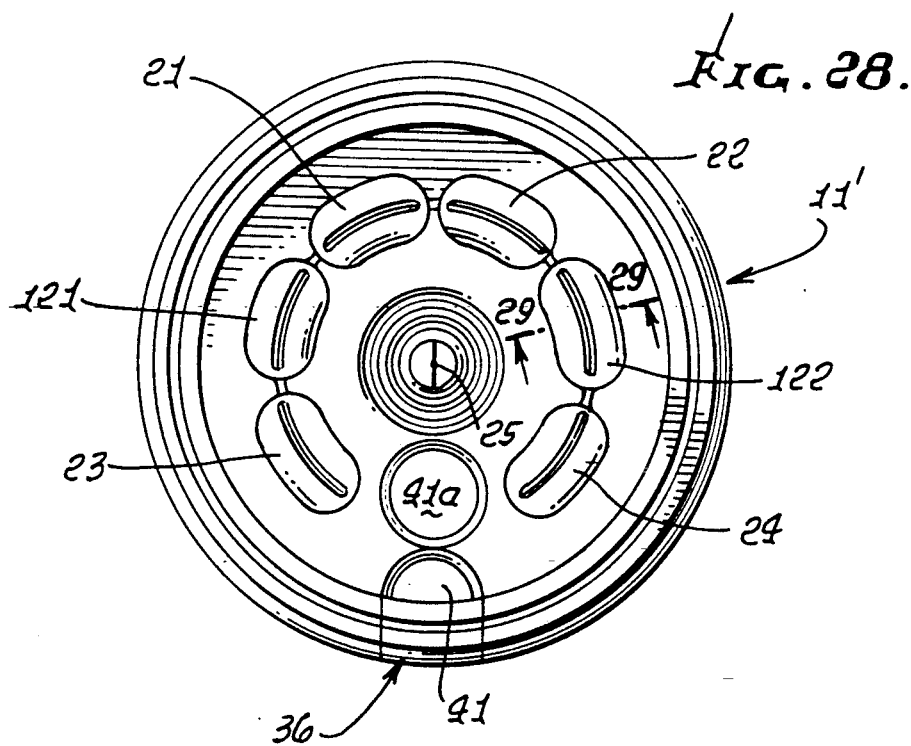
FIG. 28 is a view like FIG. 2 showing yet another modification.

FIGS. 20 and 21 show a cluster of linear, elongated pushers 180 above corresponding receptacle 181. There are three rows of pushers and receptacles, each row including three pushers. Lid upper section 182a supports the pushers, and lid lower section 182b supports the receptacles. A container 184 is elongated and in the form of a tray having upright walls 185. Section 182b seats on the upper rim of the walls; and section 182a has a skirt 186 that fits down over and adjacent the walls 185. Salad 189 is received in the tray, and the receptacles and pushers form zones 187 for liquid salad dressing or different dressings. Deflectors 188 are carried by the pushers and function in the same manner as described in respect of FIGS. 1–8. One may therefore dispense selected salad dressing on selected portions of the salad by operation of the pushers, each of which is selectively operable along its length, so that only the selected amount of dressing is dispensed. Note tray and lid detents at 189a and 189b.

FIGS. 22–24 show the same arrangement as in FIGS. 20 and 21 except that the food in the transparent plastic tray 191 comprises a frankfurter (hot dog) 190 in an open bun 190a. The lid sections 192a and 192b are arched, as shown, and there are three rows of pushers 194 and receptacles 195, for example to contain mustard, in the row of receptacles 195a, catsup in receptacles 195b, pickle relish in receptacles 195c, and other substances, as for example minced onions, in receptacles 195d. A cord 196 is attached to an end extension 192a' of the lid 192 for transporting the closed assembly. The carrier or lid 192 is removable off the tray 191, after dispensing the substances from the receptacles by operation of the pushers to enable removal of the bun o frankfurter for consumption. Deflectors appear at 197.

FIGS. 25 and 26 are like FIGS. 20 and 21 except that the food in the container 200 comprises ice cream at 210. Note the cherry 201 positioned at the top center of the frozen ice cream, as by a downward bulge 203 on the cover 204. The latter carries elongated pushers 205 and receptacles 206 that extend circularly on the cover, and define zones 207 for reception of toppings, as desired (chocolate sauce, etc.). Note deflectors 209 carried by the pushers.

In FIG. 27, a flat tray 211 supports multiple of the containers 200, as described.

In FIGS. 28-31, the elements are closely similar to those seen in FIGS. 2, 3 and 6, and corresponding elements bear the same numbers. Note, however, that the arcuate lengths of the pusher and receptacles are reduced, so that less sugar, cream, etc., is contained by each pair of pusher-receptacle elements. Also, an additional two pairs of such elements are provided—see pushers 121 and 122, for example.

Figure 29:
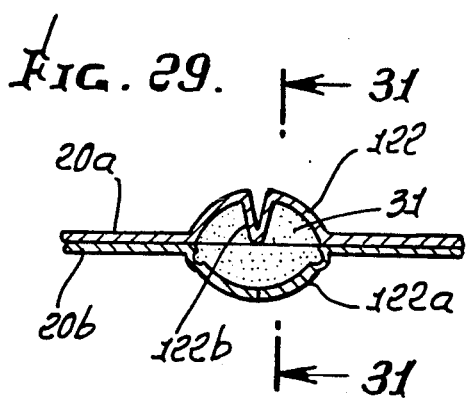
FIG. 29 is an enlarged section taken on lines 29—29 of FIG. 28.
Figure 30:
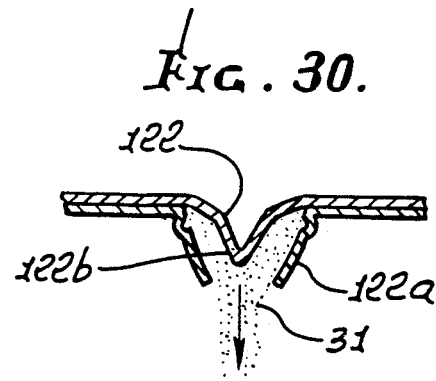
FIG. 30 is a view like FIG. 6 showing the FIG. 29 receptacle in downwardly opened position.

FIGS. 29 and 30 indicate that the added pusher and receptacle 122 and 122a are the same in cross section as the pusher and receptacle elements, as seen in FIGS. 3 and 6, and are openable in the same manner.

Figure 31:
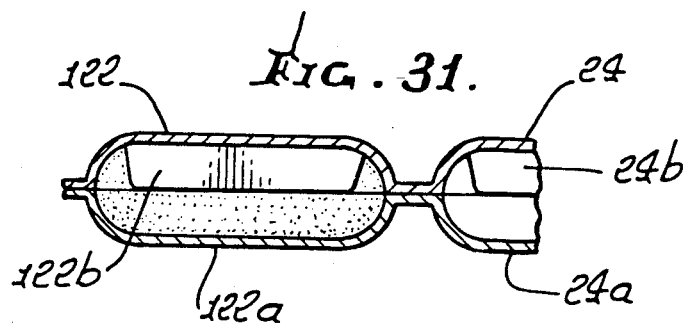
FIG. 31 is a section taken along the length of a succession of pushers and receptacles of the type seen in FIG. 28.

FIG. 31 shows the close spacing of successive pusher and receptacle elements.

The above cups, caps, sticks, etc., can be made of recyclable material, such as PVC, polystyrene, or oriented polystyrene (OPS), each being of food grade, FDA approved.

In FIG. 5, the cover sections 41 and 41a may snap together at 41b. In FIG. 4, the lowermost wall portion of receptacle 55 may contain one or more through openings, as at 55c, to pass air or water vapor to the exterior. The lids may also contain such openings.

In FIG. 14, the opening at 134 can take the form of opening 49a in FIG. 8. In FIG. 3, the sugar and cream contents 30 and 31 can partly fill the spaces between the pushers and receptacles, instead of completely filling them.

In FIG. 12, the mixing stick 59 may contain coffee or tea in one end portion, and sugar in the opposite end portion, so that a user can selectively dip either end of the stick into hot water, to dispense the desired amount of these substances into the hot water in a cup.

Also, cream 200 can be encapsulated between the coffee or tea) 201 and the sugar 202 as per FIG. 12a, and the user can optionally break the stick at that point and pour the cream into the cup. The structure shown in fragmentary FIG. 12a is meant to embody these features. See frangible capsule 204, for cream, in the intermediate portion of the stick 58b', which is like stick 58b.

Referring to FIGS. 32 and 33, a medicament dispenser 220 includes a carrier means 221 having top wall 222, side and end walls 223 and 224, and flap means 225 connected at 226 to the side and end walls or body portions. The flap means extending in a plane parallel to the user's skin or other surface 227. That surface may alternatively comprise a bandage (gauze for example) over the user's skin 227'. Thin flap 225 and the described walls may consist of plastic material. Adhesive layer 228 is carried at the underside of the flap to adhere to 227.

Figure 35:
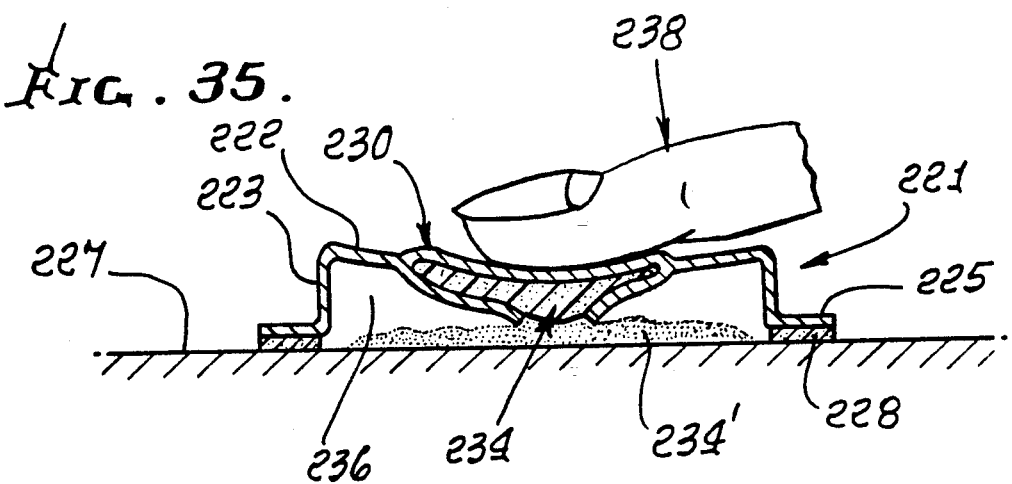
FIG. 35 is a view like FIG. 33 showing deflection of the pusher, to squeeze the dispenser sponge.

An elongated, upwardly domed pusher 230, and a receptacle 231 under the pusher, are integral with the top wall 222, as show, i.e., are carried by the carrier means 221, which acts as a holder. An elongated zone 233 is formed between 230 and 231 to receive a dispensable (flowable) medicament 234'. The latter may be carried as within a porous synthetic resin sponge 234, to be dispensed when the sponge is squeezed by downward deflection of the pusher, and when the receptacle 231 is deflected downwardly, as in FIG. 35, to pass the medicament from the sponge to the space 236 below wall 222, and onto surface 227. See the dispensed medicament 234' in FIG. 35, spread over the skin or other surface 227; and the user's finger 238 pressing downward on the flexible pusher 230 to locally deflect it downwardly, locally squeezing the sponge 234 and deflecting the receptacle. The latter opens up a normally closed slit or joint 239 to pass the medicament into space 236. Other portions of the sponge (along its length), not beneath the user's finger, are not squeezed sufficiently to dispense the medicament. See for example FIG. 32 showing different pusher areas or zones A-D to be selectively pushed, and corresponding sponge zones A'-D' in FIG. 34. Thus, if carrier portion A is pushed, the medicament in sponge portion A' is dispensed, but not the medicament in sponge portions B'-D'. Pusher areas A-D may be isolated from one another by slitting along perforated lines 250.

The sponge portions A'-D' may carry different flowable medicaments so that the user can effect dispensing of any selected medicament, as desired, without removal of the carrier 221 from the user's skin. And, he may tilt his skin zone to effect flowing of the medicament lengthwise of the carrier, in space 236, to treat the skin beneath that space 236, as after upward spring-back of the resilient carrier and its walls, as well as the resilient walls of the pusher and receptacle. Thus, a combination medicament treatment can also be achieved, with selected medicaments, mixing occurring by tilting after dispensing, as referred to. Merely as illustrative, such medicaments may include treatment liquid, lotion, cream, cold water, boric acid solution, antiseptic solution, ointments, etc. Many others are possible.

Figure 36:
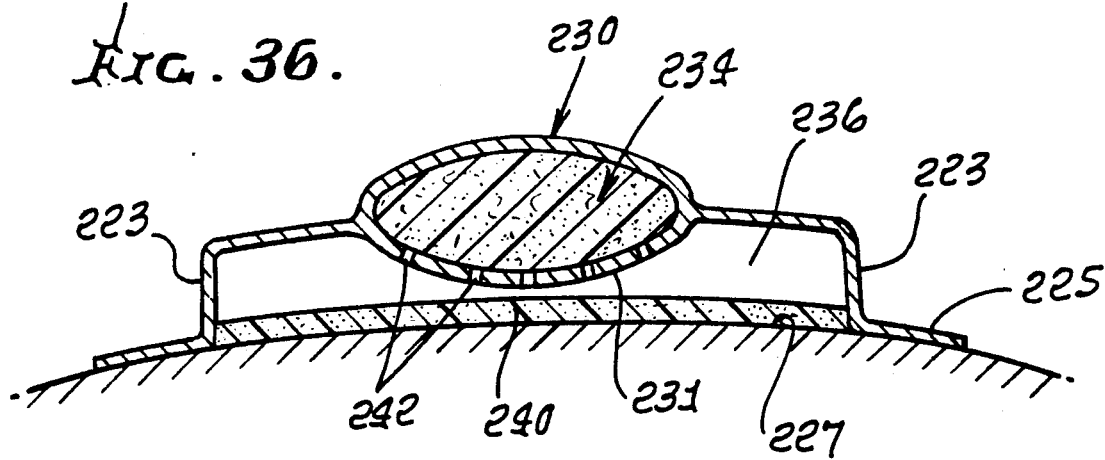
FIG. 36 is a section like FIG. 33 showing the inclusion of a dispenser sponge and perforated receptacle means.

FIG. 36 is like FIG. 33; however, an additional sponge 240 is located in space 236 and extends crosswise between lower extents of side walls and end walls 223 and 224. It receives the dispensed medicament from the receptacle, and holds it in moistening contact with the skin 227. Sponge 240 may also serve as an applicator sponge. Note the small through-openings 242 in the receptacle layer 231 to pass the medicament when sponge 234 is squeezed between 230 and 231. Sponge 240 is elongated to the same or about the same extent as sponge 234, and retained by walls 223 and 224. Layer 231 may be regarded as porous, when deflected. It may be a permeable or semi-permeable membrane, and osmotic flow of medicament may occur or be provided.

Figure 37:
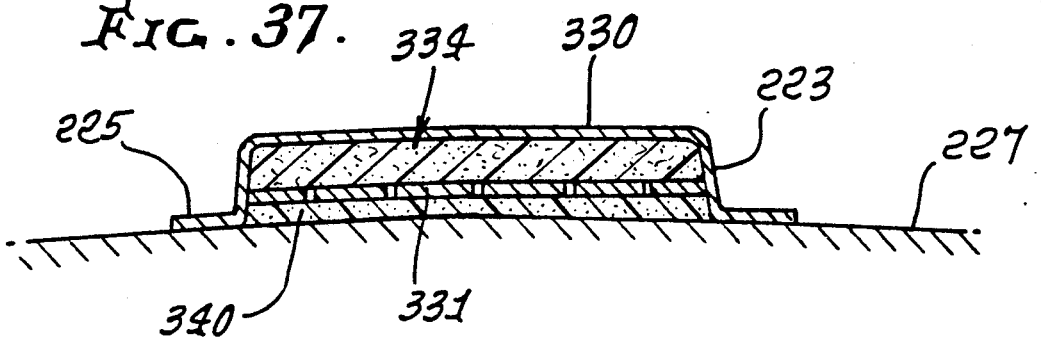
FIG. 37 is a view like FIG. 36 showing a modification.

Another similar configuration is seen in FIG. 37, with pusher 330, receptacle 331, medicament retainer sponge 334, and applicator sponge 340 arranged in layered, generally parallel relation for compactness.

Figure 38:
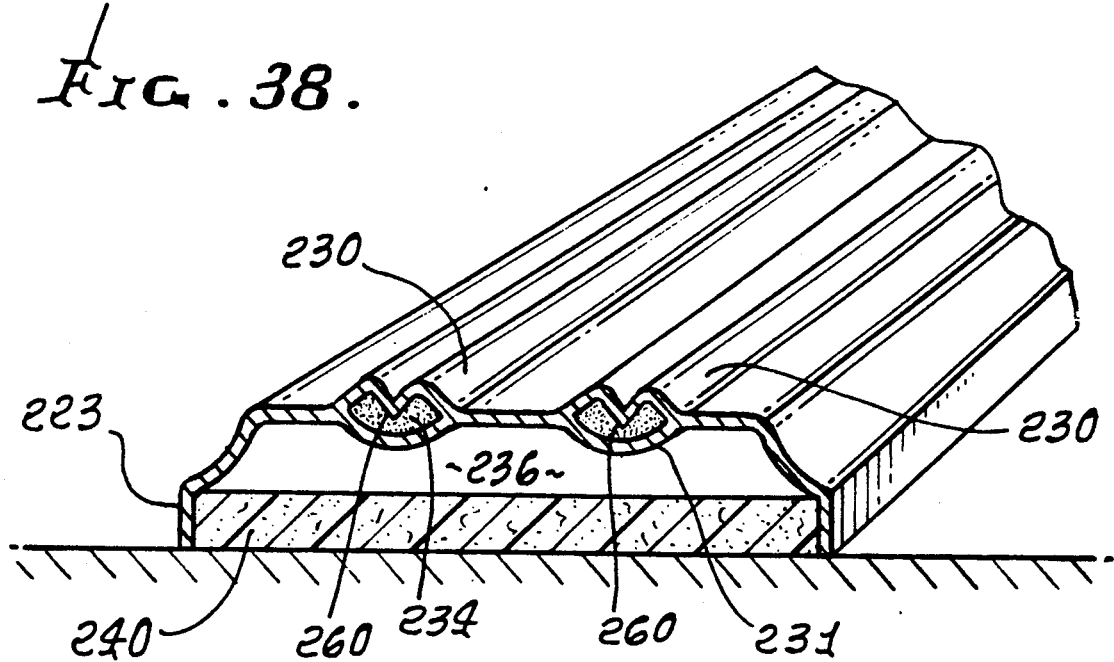
FIG. 38 is a view like FIG. 33 showing yet another modification.
Figure 39:
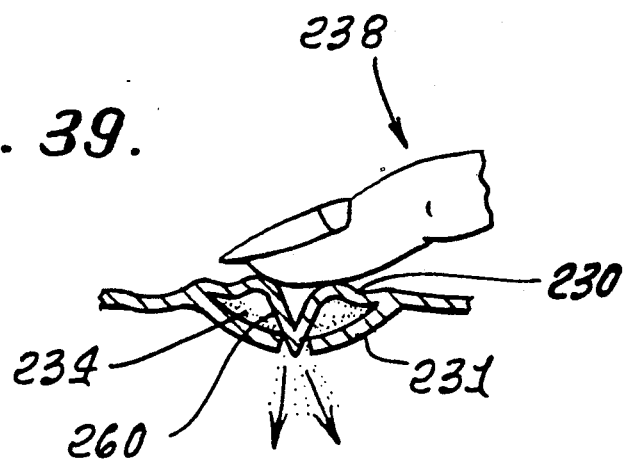
FIG. 39 is a section showing operation of the FIG. 38 system to effect penetration of the receptacle means by penetrator structure carried by the deflected pusher means.

In FIGS. 38 and 39, the elements are the same as in FIG. 36; however, multiple pusher and receptacles are shown. Each pusher has a V-shaped penetrator 260 like that at 23b in FIG. 3, with tapered side walls, and is adapted to penetrate the receptacle when pushed downwardly. See FIG. 39. Multiple such penetrators may be employed along each pusher length, and corresponding to different zones, as at A-D in FIGS. 32 and 34, to locally penetrate the receptacle, as selected. No flaps 225 are employed, and the device of FIGS. 38 and 39 may be used as an applicator, i.e., moved along the skin to apply medicament (in sponge 240) to different areas of the skin.

In accordance with additional features of the invention, the pusher structure includes at least one elongated pusher having length which is typically at least about three times its width, and having arching extent over its width so as to project upwardly from the carrier structure; and a deflector means may be employed to be integral with the arching extent to project downwardly in the arching extent toward the receptacle structure, along the elongated length of the pusher in response to downward deflection of the pusher structure, whereby a user can progressively run his finger lengthwise along the pusher to deflect the pusher variably along its length and to an extent corresponding to the amount of dispensable medicament substance to be dispensed from the receptacle structure, in response to deflector effected passage of the medicament substance via the receptacle structure.

Figure 40:
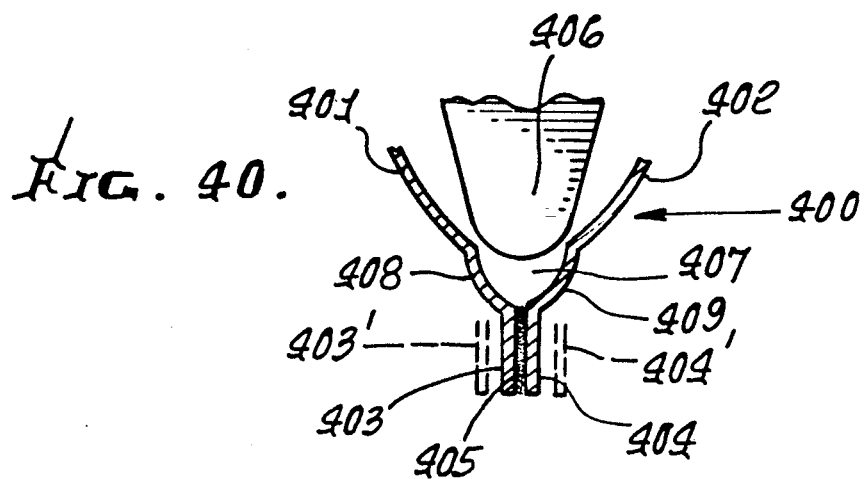
FIG. 40 is an enlarged view of a penetration assembly.

In FIG. 40, a receptacle means 400 has sections 401 and 402 which are cup-shaped, and provided with two facing flanges 403 and 404. The latter are lightly held together in closed condition, as by adhesive 405. When the penetrator 406 on the pusher descends into cup-shaped space 407 and then below that, it tends to exert force on walls 408 and 409 which in turn tend to displace the flanges 403 and 404 apart, as to spread positions 403' and 404' indicated in broken lines. This, then, allows flow of medicament past and between the separated flanges, as toward an associated applicator. Walls 401 and 402 are resilient, and tend to return to non-spread positions when the penetrator 406 is lifted, allowing the flanges to close together to shut off flow of medicament.

Figure 41:
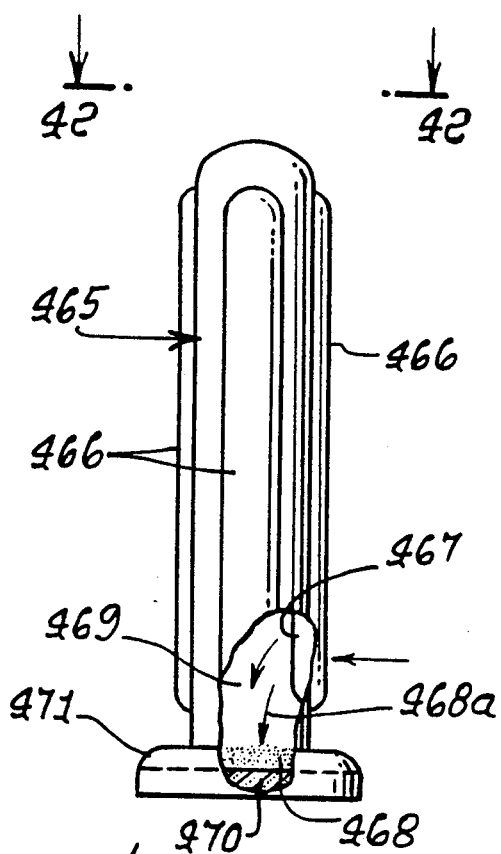
FIG. 41 is an elevation, partly in section, showing an applicator having a hollow handle with associated dispensing means.
Figure 42:
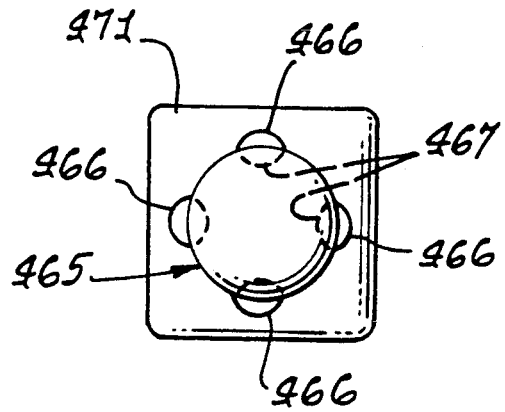
FIG. 42 is an end view taken on lines 42—42 of FIG. 41.

In FIGS. 41 and 42, a hollow, elongated handle 465 carries four elongated, deflectable pushers 466 and four elongated receptacles 467 laterally beneath the respective pushers. When a user's finger is selectively run along a pusher, it controllably and locally deflects the pusher inward to displace medicament 468 inwardly of and from a receptacle 467, and into the handle hollow 469. See arrows 468a. The medicament then falls onto the applicator 470, which may comprise a sponge applicable to the user's skin. Note holder 471 attached to one end of the handle and retaining the sponge in position.

Figure 43:
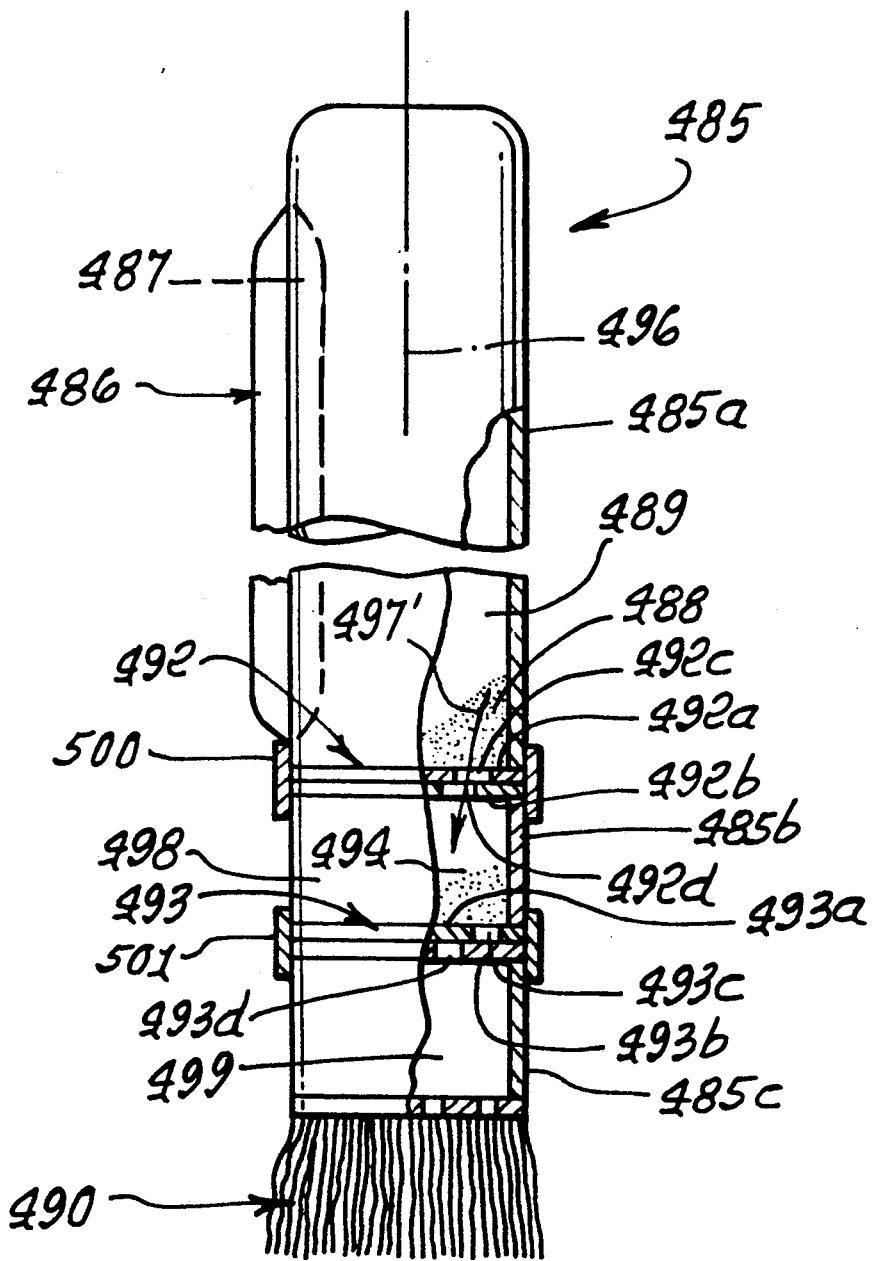
FIG. 43 is an elevation, partly in section, showing an applicator having a modified hollow handle with associated dispensing means, and gating means to controllably gate medicament flow toward the applicator.

In FIG. 43, a hollow, elongated handle 485 carries one elongated, laterally deflectable pusher 86, and one elongated receptacle 487 beneath that pusher. When a user's finger is selectively run along the pusher, it controllably and locally deflects the pusher inward to locally deflect medicament 488 inwardly of and from receptacle 487, and into the handle hollow 489. That medicament may, for example, consist of powder (say, talcum) that flows to a powder puff 490 made up of random strands of flexible material, such as yarn or the like, for controllable application and spreading into the user's skin.

Also provided is gate means between the hollow interior of the handle and the applicator, for gating the flow of medicament to the applicator. The gate means may include relatively movable gate elements. First and second gates may be employed, and spaced apart to define a chamber therebetween, whereby medicament may be gated into the chamber in measured amount, via the first gate, and the measured amount of medicament may be gated out of the chamber and via the second gate, toward the applicator. See for example first gate 492 above a second gate 493, with a measurement chamber 494 therebetween. Gate elements 492a and 492b may be relatively movable about axis 496 to bring openings 492c and 492d into registration, to allow medicament to flow through those gates (see arrow 497') into chamber 494 in measured amount (wall 498 of 494 may be transparent and scored to allow visual observation of the fill of medicament into 494). Thereafter, gate elements 493a and 493b may be relatively rotated about axis 496 to bring their openings 493c and 493d into registration, allowing discharge of the measured amount of medicament into space 499, and into the puff, as referred to. Handle tubular parts 485a, 485b and 485c may be relatively rotated to achieve relative rotation of the gate elements, as referred to; thus, gate disc 492a may be attached to 485a; and gate discs 492b and 493a may be attached to 485b; and gate disc 493b may be attached to 485c. Note retainer rings 500 and 501 on the handle.

I claim:

1. In a medicament dispenser, to dispense medicament onto a user's surface, the combination comprising
    a) carrier means having a dome portion,
    b) elongated pusher means on the carrier means,
    c) elongated receptacle means beneath the pusher means and on the carrier means, there being an elongated zone between the pusher means and receptacle means to receive dispensable medicament substance or substances,
    d) the pusher means being selectively manually deflectable toward the receptacle means, at selected locations along pusher means length,
    e) the receptacle means having selected lengthwise locations corresponding to said selected pusher means locations that are rendered porous in response to deflection of the pusher means toward the receptacle means and including said medicament substance or substances in said zone,
    f) whereby dispensing of dispensable medicament substance or substances occurs at locations on said receptacle means corresponding to said selected deflected locations of the pusher means toward the receptacle means,
    g) the pusher means and receptacle means being on said dome portion of the carrier, said zone adapted to receive and confine the medicament substance, and wherein there is a medicament-containing sponge between the receptacle means and the pusher means, the sponge being elongated,
    h) there being a space in the carrier at a side of the receptacle means, wherein an applicator sponge is positioned in said space to receive medicament substance via the porous receptacle when the pusher means is pushed toward the receptacle means.

2. The combination of claim 1 wherein both said sponges are elongated in the direction of pusher means elongation, for squeezing of the medicament-containing sponge and for feeding of medicament of the medicament-containing sponge to the applicator sponge.

3. The combination of claim 1 wherein there are deflector means integral with the pusher means, projecting toward the receptacle means to deflect and open the receptacle means in response to deflection of the pusher means toward the receptacle means, thereby to allow passage of medicament substance to the user's surface.

4. The combination of claim 3 wherein said deflector means includes walls which taper toward the receptacle means to define an elongated penetrator.

5. The combination of claim 1 including medicament substances between the pusher and receptacle, and along the lengths thereof.

6. In a dispenser for dispensing dispensable medicament substance or substances, the combination comprising
    a) carrier structure,
    b) elongated pusher structure on the carrier structure,
    c) elongated receptacle structure beneath the pusher structure and on the carrier structure, there being an elongated zone between the pusher structure and receptacle structure to receive dispensable medicament substance or substances and including said medicament substance or substances in said zone, d) the pusher structure being selectively manually deflectable toward the receptacle structure, at selected locations along the length of the pusher structure length, e) the receptacle structure having selected lengthwise locations corresponding to said selected locations along the length of the pusher structure that are rendered porous to pass the medicament substance in response to deflection of the pusher structure, toward the receptacle structure, f) whereby dispensing of the dispensable medicament substance or substances occurs at said selected lengthwise locations of the receptacle structure, g) the pusher structure including at least one elongated pusher having length which is at least about three times its width, and having arching extent over its width so as to project away from the receptacle structure, and including a deflector means integral with said arching extent to project in said arching extent toward the receptacle structure, along the elongated length of the pusher in response to said deflection of the pusher structure, whereby a user can progressively run his finger lengthwise along the pusher structure to deflect the pusher structure variably along its length and to an extent corresponding to the amount of dispensable medicament substance to be dispensed from the receptacle structure, and in response to deflector effected passage of the medicament substance via the receptacle structure.

7. The combination of claim 6 including said medicament between the pusher and receptacle.

8. The combination of claim 7 wherein said medicament consists of powder.

* * * * *